US00PP11232P

United States Patent [19]

Kordes

[11] Patent Number: Plant 11,232

[45] Date of Patent: Feb. 22, 2000

[54] MINIATURE ROSE PLANT NAMED 'KORKLEIVA'

[75] Inventor: Wilhelm Kordes, Sparrieshoop, Germany

[73] Assignee: Bear Creek Gardens, Inc., Medford, Oreg.

[21] Appl. No.: 09/046,313

[22] Filed: Mar. 23, 1998

[51] Int. Cl.[7] ..... A01H 5/00

[52] U.S. Cl. ..... Plt./116

[58] Field of Search ..... Plt./116, 117, 118, Plt./123, 124, 125

*Primary Examiner*—Howard J. Locker

*Attorney, Agent, or Firm*—Klarquist Sparkman Campbell Leigh & Whinston, LLP

[57] ABSTRACT

Miniature rose plant having an ability to root easily from softwood cuttings and to flower quickly with novel flower color; long lasting flowers; vigorous growth habit; and resistance to powdery mildew.

1 Drawing Sheet

The present invention relates to a new and distinct variety of rose plant of the miniature class which was originated by me by crossing the variety 'KORtexung', U.S. Plant Pat. No. 6,513, with an unnamed seedling.

The primary objective of this breeding was to produce a new miniature rose variety having a compact, well branched growth habit; long shelf life; novel, stable flower color; ability to root quickly and easily from softwood cuttings; ability to flower quickly; and resistance to powdery mildew. The objective was substantially achieved, along with other desirable improvements, as evidenced by the following unique combination of characteristics that are outstanding in the new variety and that distinguish it from its parents, as well as from all other varieties of which I am aware:

1. Very long shelf life of potted plants, i.e., plants remain in bloom over a very long period of time;
2. Easy to root from softwood cuttings;
3. Vigorous growth habit;
4. Flowers quickly from cuttings;
5. Resistance to powdery mildew; and
6. Novel flower color.

Asexual reproduction of this new variety by cutting propagation, as performed at Sparrieshoop, Germany, and Wasco and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'Kortexung' (U.S. Plant Pat. No. 6,513).

*Pollen Parent.*—Unnamed seedling.

Classification:

*Botanical.*—Rosa hybrida.

*Commercial.*—Miniature rose.

FLOWER

Observations made from specimens grown in a greenhouse environment at Sparrieshoop, Germany and Somis, Calif. from January, 1996 to December, 1997.

Blooming habit: Continuous.

Bud:

*Size.*—Three-quarters inch when the petals start to unfurl.

*Form.*—The bud form is long, pointed ovoid.

*Color.*—When sepals first divide, bud color is Orange-White Group 159C with petal tips Green-White Group 157B. When half blown, the upper sides of the petals are Yellow-White Group 158B on the exposed petals; the upper sides of the interior petals are Yellow-Orange Group 16C; and the lower sides of the petals are Orange-White Group 159C.

*Sepals.*—Color: Green group 138B. Surface texture: Covered in fine hairs. There are three lightly appendaged sepals. There are two unappendaged sepals with hairy edges.

*Receptacle.*—Color: Green Group 146C. Shape: Funnel. Size: Small (3/8"×5/16"). Surface: Smooth.

*Peduncle.*—Length: Short (1¼"). Surface: Glandular. Color: Green Group 137A. Strength: Stiff, erect.

Bloom:

*Size.*—Small. Average open size is 1½ to 1¾ inches.

*Borne.*—Singly.

*Stems.*—Short, strong. Average length is about five inches.

*Form.*—When first open: High centered. Permanence: Retains its form to the end, outer petals curl back.

*Petalage.*—Number of petals under normal conditions: 25–30.

*Color.*—The upper sides of the petals are Yellow-White Group 158B on the outer exposed petals; the upper sides of the interior petals are Yellow Group 16C. The reverse sides of the petals are Orange-White Group 159C. The base of each petal has a small (3/16"×3/16"), Yellow Group 4A, half moon at the point of attachment. The major color on the upper sides is Yellow-White Group 158B.

*Variegations.*—Occasional green streak on the guard petals.

*Discoloration.*—At the end of the first day: No change. At the end of the third day: No change. By day five or six, as the flower opens, the interior petals change from Yellow-Orange Group 16C to Yellow-White Group 158B. This color remains stable until day 18 to day 20 when the color changes to Green-White Group 157B. Petals finally drop after day 25.

*Fragrance.*—None.

Petals:

*Texture.*—Thick, leathery.

*Shape.*—Round.

*Form.*—Tips slightly recurved.

*Arrangement.*—Imbricated. Petaloids in the center are few (0–7) and small (5 to 8 mm long and from 3 to 4 mm wide). Petaloids are Yellow Group 16C on their upper surface and Orange White Group 159C on their lower surface.

*Persistence.*—Petals drop off cleanly before drying.

*Lastingness.*—On the plant: Very long (25 days). As a cut flower: Very long (25 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Reddish.

*Stigmas.*—Color: Greenish-White.

Plant:

*Form.*—Bush.

*Growth.*—Vigorous; upright; branching; compact. Grown in a 4" pot, a mature plant is 6–8" in height and 5–6" in width.

Foliage: Number of leaflets on normal mid-stem leaves: Five.

*Size.*—Small (3" long×2" wide).

*Quantity.*—Abundant.

*Color.*—New foliage: Upper and lower surfaces: Greyed-Red Group 178C. Old foliage: Upper surface: Green Group 139A. Lower surface: Green Group 139C.

*Shape.*—Pointed oval.

*Texture.*—Upper side: Semi-glossy, smooth.

*Edge.*—Serrated.

*Serration.*—Single, small.

*Petiole rachis.*—Color: Greyed-Purple Group 183B.

*Petiole underside.*—Smooth with occasional prickles.

*Stipules.*—Short (5/16"), serrated, bearded.

*Disease Resistance.*—Resistant to mildew under normal growing conditions in the greenhouse at Sparrieshoop, Germany and Somis, Calif.

Wood:

*New Wood.*—Color: Greyed-Purple Group 183B. Bark: Smooth.

*Old Wood.*—Color: Green Group 137B. Bark: Smooth.

Prickles:

*Quantity.*—On main canes from base: Few. On laterals from main canes: Few.

*Form.*—Short, straight to hooked slightly downward.

*Color when young.*—Greyed-Purple Group 183D.

*Color when mature.*—Greyed-Orange Group 168D.

Small prickles:

*Quantity.*—On main stalks: None. On laterals: None.

I claim:

1. A new and distinct variety of miniature rose plant as herein shown and described characterized particularly by its ability to root easily from softwood cuttings and to flower quickly; its novel flower color and long lastingness of its flowers; its vigorous growth habit; and resistance to powdery mildew.

* * * * *

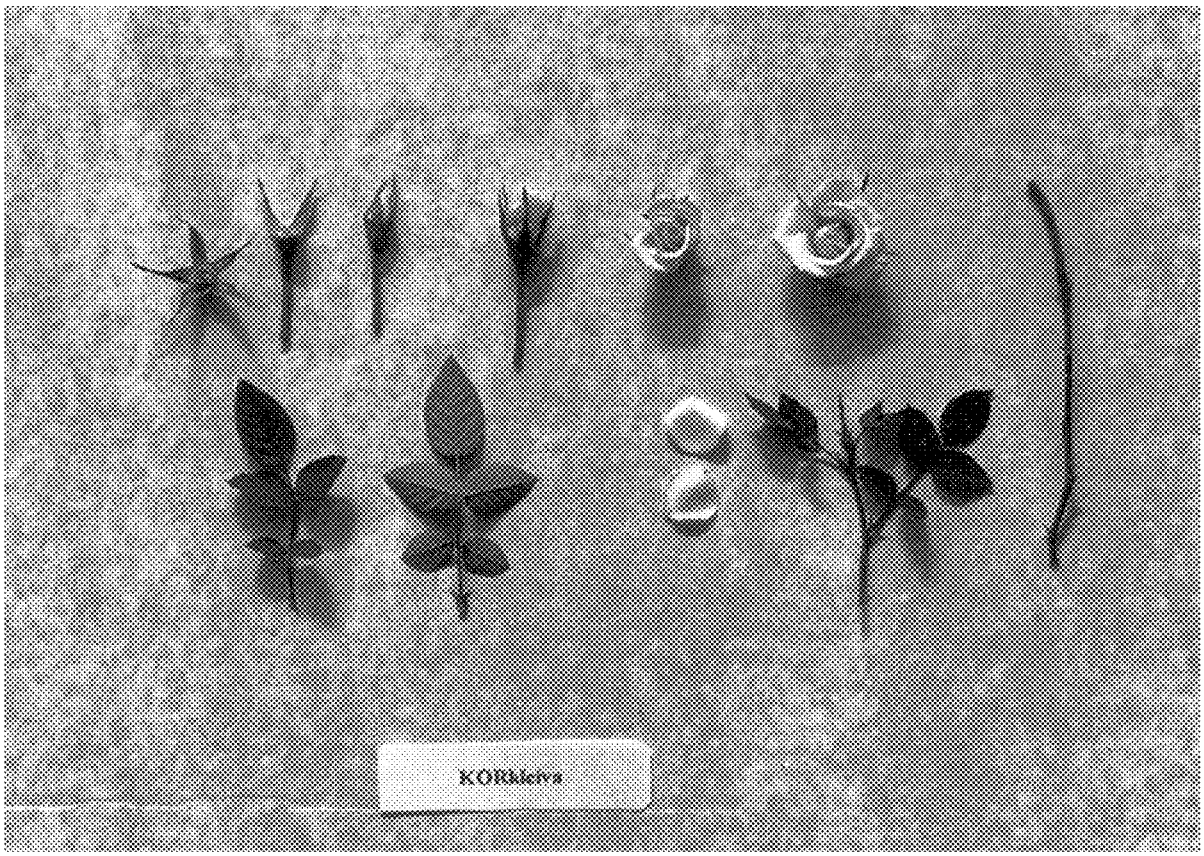
KORkleva